(12) United States Patent
Neville

(10) Patent No.: US 11,931,501 B2
(45) Date of Patent: Mar. 19, 2024

(54) DIALYSIS SHEATH FOR USE IN ACCESSING A DIALYSIS ARTERIOVENOUS GRAFT OR FISTULA AND METHODS OF USE

(71) Applicant: Evan T. Neville, Swansea, IL (US)

(72) Inventor: Evan T. Neville, Swansea, IL (US)

(*) Notice: Subject to any disclaimer, the term of this patent is extended or adjusted under 35 U.S.C. 154(b) by 0 days.

(21) Appl. No.: 18/342,447

(22) Filed: Jun. 27, 2023

(65) Prior Publication Data

US 2024/0009370 A1    Jan. 11, 2024

Related U.S. Application Data

(60) Provisional application No. 63/367,849, filed on Jul. 7, 2022.

(51) Int. Cl.
*A61M 1/36* (2006.01)
*A61M 25/00* (2006.01)
*A61M 25/10* (2013.01)

(52) U.S. Cl.
CPC ...... *A61M 1/3661* (2014.02); *A61M 25/1002* (2013.01); *A61M 2025/0019* (2013.01); *A61M 2025/109* (2013.01)

(58) Field of Classification Search
CPC ...... A61M 2210/12; A61M 2202/0413; A61M 2202/021; A61M 2205/053; A61M 1/3472; A61M 1/3681; A61M 1/34; A61M 1/3661; A61M 25/1002; A61M 2025/0019; A61M 2025/109

See application file for complete search history.

(56) References Cited

U.S. PATENT DOCUMENTS

| | | |
|---|---|---|
| 6,547,820 B1 | 4/2003 | Staudenmeier |
| 6,663,590 B2 | 12/2003 | Blatter |
| 7,214,228 B2 | 5/2007 | Crabtree |
| 7,214,301 B2 | 5/2007 | Thorstensen |
| 7,553,326 B2 | 6/2009 | Sweet |
| 7,833,186 B1 | 11/2010 | Batiste |
| 8,114,044 B2 | 2/2012 | Cul |
| 8,858,486 B2 | 10/2014 | Zhang |

(Continued)

OTHER PUBLICATIONS

Medtronic; "U.S. Aortic product catalog"; copyright 2022 (58 pages).

(Continued)

*Primary Examiner* — Leslie R Deak
(74) *Attorney, Agent, or Firm* — Nixon Peabody LLP

(57) ABSTRACT

A dialysis sheath is used with a catheter that cleans clots from a synthetic blood vessel or fistula. The dialysis sheath comprises a main hollow body and a stop mechanism. The main body has a lower portion for insertion into the synthetic blood vessel or fistula. The stop mechanism is movable between (i) a first position in which the stop mechanism is adjacent to or within a surface of the main hollow body and (ii) a second position in which the stop mechanism radially protrudes from the main hollow body. The stop mechanism is configured to engage an inner surface of the synthetic blood vessel or fistula to maintain the lower portion of the dialysis sheath within the synthetic blood vessel or fistula when the dialysis sheath is moved to a different position. The stop mechanism can be fluid-actuated and include a balloon-like structure.

20 Claims, 8 Drawing Sheets

(56) References Cited

U.S. PATENT DOCUMENTS

| | | |
|---|---|---|
| 8,900,177 B2 | 12/2014 | Batiste |
| 9,585,998 B2 | 3/2017 | Gage |
| 9,782,533 B2 | 10/2017 | Brenneman |
| 9,907,900 B1 | 3/2018 | Batiste |
| 10,307,242 B2 | 6/2019 | Walzman |
| 10,889,898 B2 | 1/2021 | Ren |
| 11,376,403 B2 | 7/2022 | Pillai |
| 11,389,622 B1 | 7/2022 | Rayhanabad |
| 11,511,020 B2 | 11/2022 | Ryan |
| 2004/0215125 A1 | 10/2004 | Brown |
| 2008/0281249 A1 | 11/2008 | Gertner |
| 2009/0209918 A1 | 8/2009 | Berglund |
| 2010/0121247 A1 | 5/2010 | Yang |
| 2011/0229549 A1 | 9/2011 | Nugent |
| 2013/0150767 A1 | 6/2013 | Tsyrulnykov |
| 2013/0158483 A1 | 6/2013 | Senitko |
| 2013/0331928 A1 | 12/2013 | Yang |
| 2013/0338562 A1 | 12/2013 | Williams |
| 2015/0265393 A1 | 9/2015 | Stonebridge |
| 2017/0231565 A1 | 8/2017 | Olivarez |
| 2017/0252447 A1 | 9/2017 | Shebuski |
| 2018/0280605 A1 | 10/2018 | Gage |
| 2019/0076146 A1 | 3/2019 | Naoum |
| 2019/0255292 A1* | 8/2019 | Osypka ............. A61M 25/0147 |
| 2021/0183268 A1 | 6/2021 | Cull |
| 2021/0267745 A1 | 9/2021 | Walzman |
| 2021/0275780 A1 | 9/2021 | Rayhanabad |
| 2021/0346586 A1 | 11/2021 | Gage |
| 2022/0104840 A1* | 4/2022 | Horowitz ........... A61M 25/1011 |
| 2022/0160060 A1 | 5/2022 | Scott |
| 2022/0395286 A1* | 12/2022 | Horowitz ......... A61B 17/22032 |
| 2023/0053637 A1 | 2/2023 | Forcella |
| 2023/0081060 A1 | 3/2023 | Raju |
| 2023/0088977 A1* | 3/2023 | Fischell ............ A61M 25/0662 |
| | | 606/192 |

OTHER PUBLICATIONS

Abbott Laboratories; "Perclose Prostyle Suture-Mediated Closure and Repair System" product data sheet; copyright Jul. 2023 (9 pages).

* cited by examiner

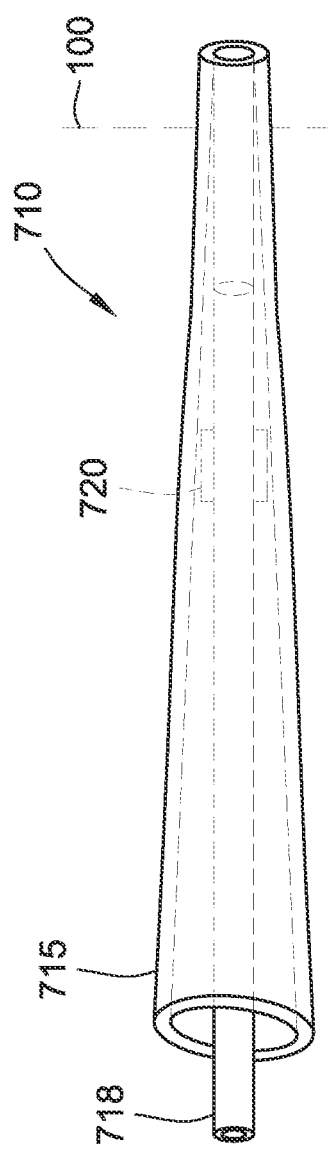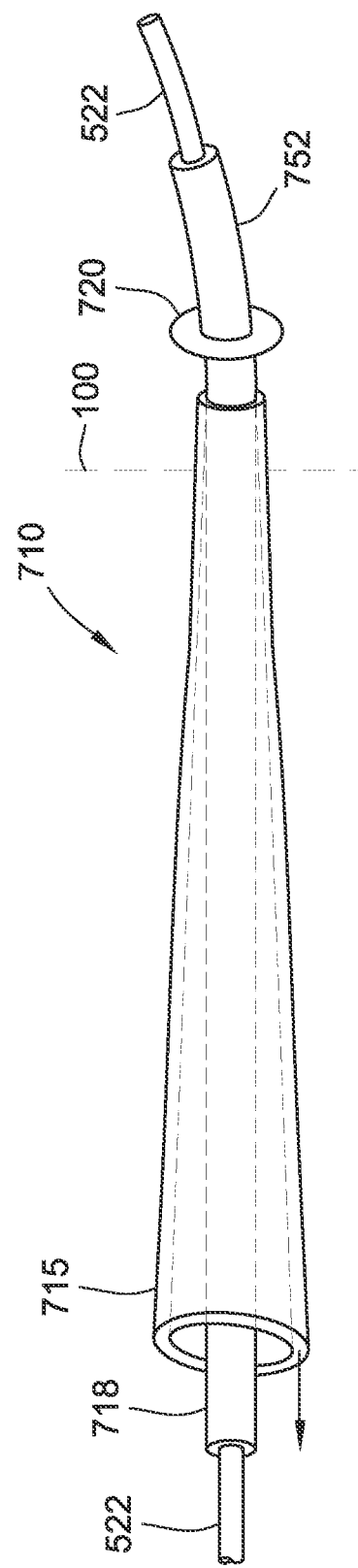
FIG. 7A
FIG. 7B

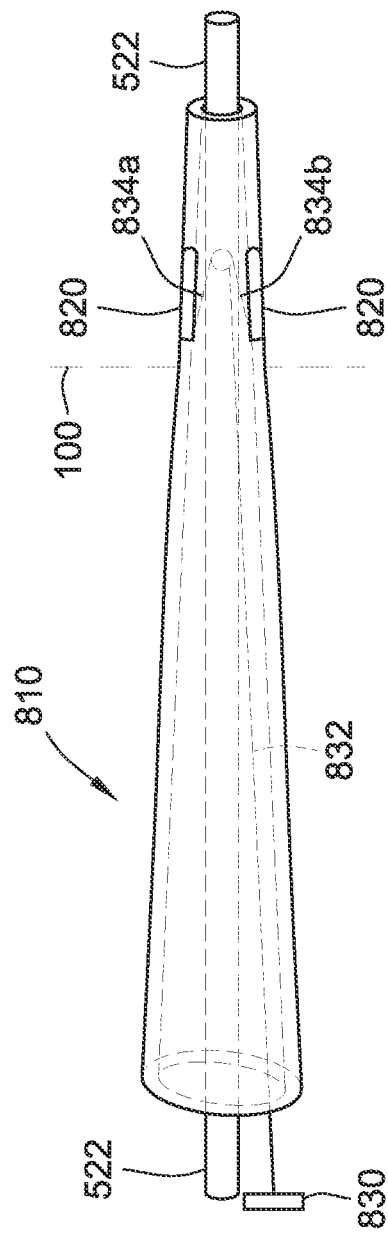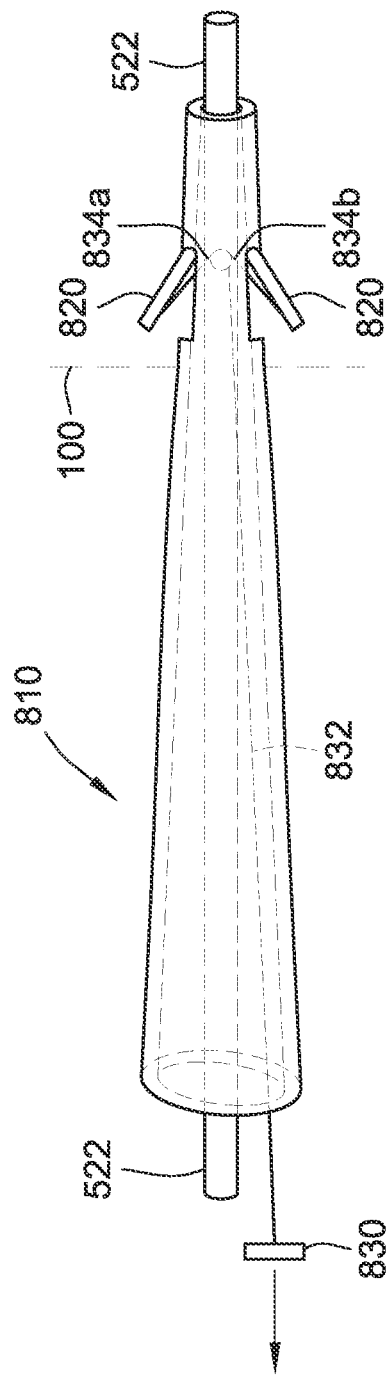

ns are often accomplished via an arteriovenous (AV) fistula or an AV graft that includes a synthetic blood vessel interposed between an artery and a vein.

DIALYSIS SHEATH FOR USE IN ACCESSING A DIALYSIS ARTERIOVENOUS GRAFT OR FISTULA AND METHODS OF USE

RELATED APPLICATIONS

The present application claims priority to U.S. Provisional Ser. No. 63/367,849, filed Jul. 7, 2022, and titled "A Shaped Separator Wire For Use With A Thrombus-Removal Catheter And A Sheath For Use With A Dialysis Arteriovenous Graft, Arteriovenous Fistula, Or Peripheral Access" which is herein incorporated by reference in its entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

The present invention generally relates to a sheath that is used for dialysis and, more particularly, to a sheath that allows for efficient access to a dialysis graft or fistula via a single access point.

BACKGROUND OF THE INVENTION

For the patients requiring dialysis, the dialysis methodology requires access to the patient's blood supply, which is often accomplished via an arteriovenous (AV) fistula or an AV graft that includes a synthetic blood vessel interposed between an artery and a vein. The dialysis involves accessing the AV graft or fistula via needles and catheters. AV grafts have a lifespan of approximately 1 to 3 years but can often last longer. However, AV grafts can be troublesome in that, when thrombosis does occur, attempts must be made in a timely fashion to successfully perform a thrombectomy on the graft or fistula. When this happens, interventional procedures are used to remove the clot and restore blood flow for dialysis.

Current percutaneous techniques of the AV graft or fistula requires a two-point access technique. One access point occurs near the arterial anastomosis in order to perform a thrombectomy of the outflow. The other access point occurs near the venous anastomosis in order to perform a thrombectomy of the arterial inflow portion of the graft or fistula. Both access points require thrombectomy devices and sheaths to work in a crisscrossing technique, which can decrease the efficacy of the thrombectomy. More importantly, with each access point of the graft or fistula, the complication rate increases. These complications include bleeding, infection, perforation, pseudoaneurysm formation, and degeneration of the graft or fistula.

As such, there is a need for avoiding the current crisscrossing technique using multiple access points to increase the efficacy of the thrombectomy and improve procedural outcomes. The present invention solves the problems associated with the current procedures by providing a new method and device that is used in conjunction with a catheter for clearing an AV graft or fistula of a clot with minimal intervention for the patient. By having only a single access point sheath with a steerable device, the complications of multiple access points will decrease in frequency. Furthermore, using a steerable device via a single access point will also save time and costs for the procedures.

The present invention also relates to new features of a separator wire that may be used in conjunction with a catheter to increase the effectiveness of removal of the clot via the suction process, but without the need for powered rotational devices that may damage the blood vessel.

All these and other objects of the present invention will be understood through the detailed description of the invention below.

SUMMARY OF THE INVENTION

In one aspect, the present invention is a dialysis sheath and a method of using a dialysis sheath as described relative to the figures.

In another aspect, the present invention is a dialysis sheath and a method of using a dialysis sheath defined by the pending claims.

In a further aspect, a dialysis sheath is for use with a catheter that cleans obstruction from a dialysis flow tube used for dialysis of a patient. The dialysis sheath comprises a main hollow body, a fluid passage, and a fluid-actuated stop mechanism. The main hollow body has a lower portion for insertion into the dialysis flow tube. The main hollow body is for guiding the catheter that enters into the dialysis flow tube for cleaning obstructions. The fluid passage extends along the main hollow body. The fluid-actuated stop mechanism is positioned within the lower portion of the main hollow body. The fluid-actuated stop mechanism is in communication with the fluid passage. The fluid-actuated stop mechanism is actuatable to transition between (i) a first position in which the stop mechanism is adjacent to or within a surface of the lower portion of the main hollow body, and (ii) a second position in which the stop mechanism expands to radially protrude away from the main hollow body so as to be configured to engage an inner surface of the dialysis flow tube to maintain the lower portion of the main hollow body within the dialysis flow tube.

In another aspect, a dialysis sheath is for use with a catheter that cleans obstruction from a dialysis flow tube used for dialysis of a patient. The dialysis sheath comprises a main hollow body and a stop mechanism. The main hollow body is for guiding the catheter that enters into the dialysis flow tube for cleaning obstructions. The stop mechanism is positioned within the lower portion of the main hollow body. The stop mechanism is actuated to transition between (i) a first position in which the stop mechanism is adjacent to or within a surface of the lower portion of the main hollow body, and (ii) a second position in which the stop mechanism radially protrudes away from the main hollow body so as to be configured to engage an inner surface of the dialysis flow tube to maintain the lower portion of the main hollow body within the dialysis flow tube. The stop mechanism may include a cam, a flexible element or plate, or a movable rod.

In another aspect, a dialysis sheath is for use with a catheter that cleans obstruction from a dialysis flow tube used for dialysis of a patient. The dialysis sheath comprises a main hollow body and a stop mechanism. The main hollow body is for guiding the catheter that enters into the dialysis flow tube for cleaning obstructions. The main hollow body has at least two slidable parts in which an inner slidable part includes the stop mechanism that fits within an outer slidable part. When the inner slidable part slides to extend beyond a lower end of the outer slidable part, the stop mechanism is exposed and transitions between (i) a first position in which the stop mechanism is adjacent to or within a surface of the inner slidable part, and (ii) a second position in which the stop mechanism radially protrudes away from the inner slidable part so as to be configured to engage an inner surface of the dialysis flow tube to maintain the main hollow body within the dialysis flow tube.

In another aspect, the present invention relates to a method of clearing a clot from a dialysis flow tube that is used for dialysis. The method comprises (i) inserting a sheath into an opening in the dialysis flow tube, (ii) inserting a catheter through the sheath for cleaning the dialysis flow tube in a first direction relative to the opening, (iii) using a fluid to expand a stop mechanism associated with the sheath such that the stop mechanism protrudes radially away from the sheath, (iv) without removing the sheath from the opening, engaging the expanded stop mechanism on an internal surface of the dialysis flow tube to assist with maintaining the sheath within the dialysis flow tube; (v) while the stop mechanism is engaging the internal surface of the dialysis flow tube, manipulating the direction of a lower portion of the sheath within the dialysis flow tube; and (vi) using the catheter to clean the dialysis flow tube in a second direction relative to the opening.

In a further another aspect, the present invention relates to a method of clearing a clot from a dialysis flow tube that is used for dialysis. The method comprises (i) inserting a sheath into an opening in the dialysis flow tube, (ii) inserting a catheter through the sheath for cleaning the dialysis flow tube in a first direction relative to the opening, (iii) using a fluid to expand a stop mechanism associated with the sheath such that the stop mechanism protrudes radially away from the sheath, (iv) without removing the sheath from the opening, engaging the expanded stop mechanism to an internal surface of the dialysis flow tube to assist with maintaining the sheath within the dialysis flow tube, and (v) while the stop mechanism is engaging the internal surface of the dialysis flow tube, manipulating the direction of the sheath within the dialysis flow tube to a second direction that is generally opposite of the first direction.

In yet a further another aspect, the present invention relates to a method of clearing a clot from a dialysis flow tube that is used for dialysis. The method comprises (i) inserting a sheath into an opening in the dialysis flow tube, (ii) inserting a catheter through the sheath for cleaning the dialysis flow tube in a first direction relative to the opening, (iii) actuating a stop mechanism associated with the sheath such that the stop mechanism protrudes radially away from the sheath, (iv) without removing the sheath from the opening, engaging the actuated stop mechanism on an internal surface of the dialysis flow tube to assist with maintaining the sheath within the dialysis flow tube, and (v) after the engaging, using the catheter within the sheath to clean the dialysis flow tube in a second direction relative to the opening.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

The present invention will be described with greater specificity and clarity with reference to the following drawings, in which:

FIG. 7A illustrates an alternative embodiment of a dialysis sheath having two portions that can release a stop mechanism that engages an inside wall of a dialysis flow tube.

FIG. 7B illustrates the alternative embodiment of FIG. 7A with the stop mechanism actuated for engaging an inside wall of a dialysis flow tube.

FIG. 8A illustrates another alternative embodiment of a dialysis sheath having a mechanical actuator that can release a stop mechanism that engages an inside wall of a dialysis flow tube.

FIG. 8B illustrates the alternative embodiment of FIG. 8A with the stop mechanism actuated for engaging an inside wall of a dialysis flow tube.

Figure 1:
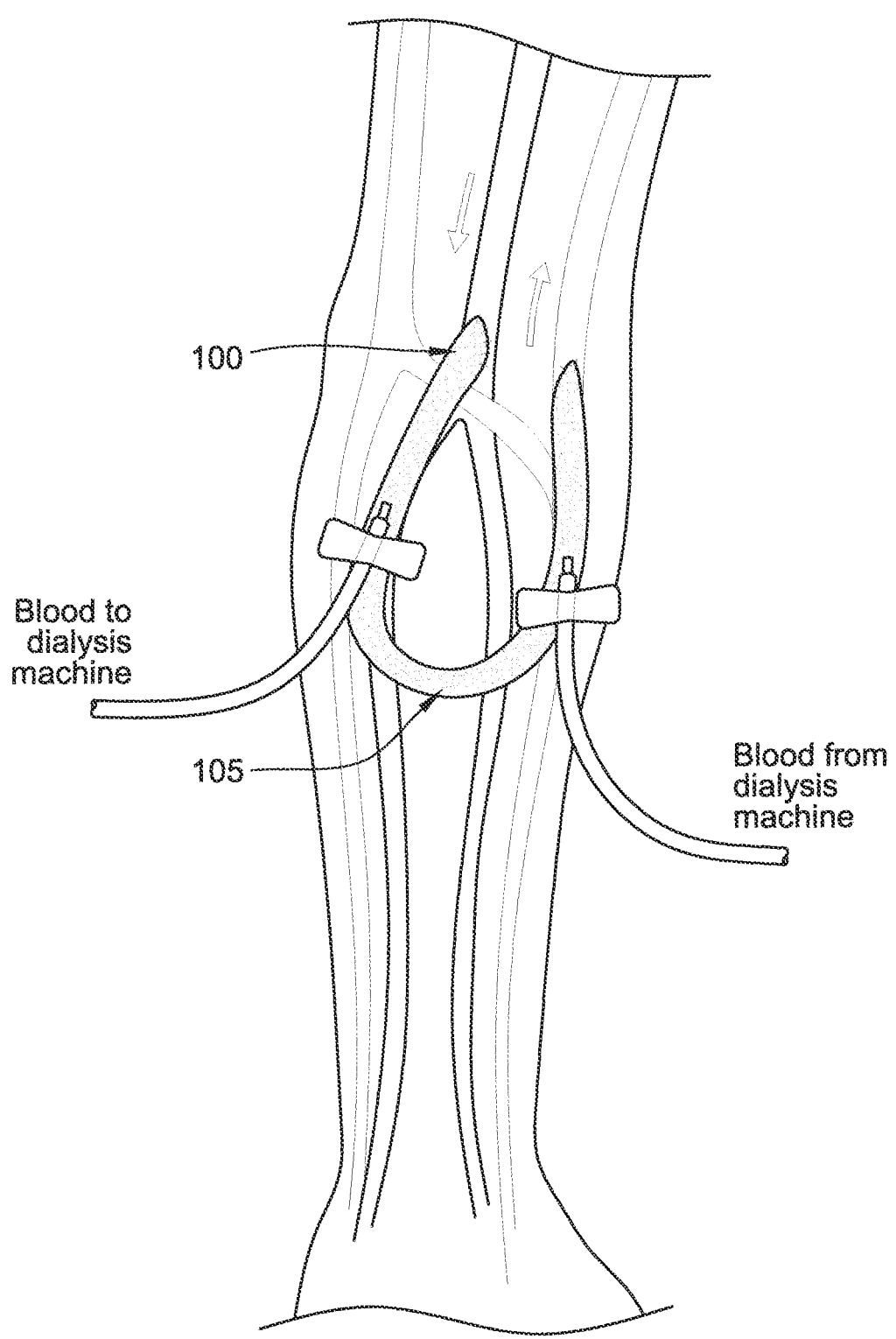
FIG. 1 schematically illustrates dialysis with use of a synthetic blood vessel in the form of a synthetic bridge graft (one type of "dialysis flow tube").

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION OF THE DRAWINGS

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

The present invention relates to removing clotting within a synthetic graft or fistula used for providing a dialysis function for a patient. As used herein, the term "dialysis flow tube" refers to any synthetic graft, synthetic blood vessel, synthetic bridge graft, or fistula that can be accessed to provide flow paths to and/or from a dialysis machine. FIG. 1 illustrates one example of a dialysis flow tube 100 (here, a synthetic bridge graft) that is under the patient's skin and placed between an artery and a vein. The dialysis flow tube 100 is typically about 15 cm to 25 cm in length and often has a curved or bent middle region 105. When the patient needs dialysis, he or she undergoes a procedure in which a professional at the dialysis center accesses the dialysis flow tube 100 under the patient's skin at two locations and two tubes are installed that transfer clean blood from and return dirty blood to a dialysis machine, as shown in FIG. 1.

The material of the dialysis flow tube 100 is susceptible to clotting that reduces blood flow. In the event of a graft thrombosis, the dialysis flow tube 100 needs to be cleaned to remove the clots. However, the current technique for removing the clot with the dialysis flow tube 100 involves the clinician inserting a catheter system in two locations near the ends of the dialysis flow tube 100 where it is grafted to the vein and the artery. When the catheter enters the artery side of the dialysis flow tube 100, it cleans toward the vein side of the dialysis flow tube 100. Conversely, when the catheter enters the vein side of the dialysis flow tube 100, it cleans in the toward the artery side of the dialysis flow tube 100, such that the overall cleaning process is two steps in a crisscrossing arrangement. As such, the currently known procedure requires at least two openings in the dialysis flow tube 100. The more openings, the higher the risk for problems in the dialysis flow tube 100.

The dialysis sheaths of FIGS. 2-7 only require a single opening in the dialysis flow tube 100 and permits the catheter to be advanced in both direction (i.e., toward the vein and toward the artery) to remove any type of obstruction, such as a thrombus. As used herein, the term "catheter" is intended to cover various types of suction catheters, mechanical catheters, and other thrombus-removal devices. In FIGS. 2A-2B, the dialysis sheath 110 includes a hollow main body 112 that includes a steerable lower portion 114 and an actuator portion 116 that can, for example, be rotated to change the direction of the steerable lower portion 114, as shown schematically in FIGS. 3A-3B.

Figure 2A:
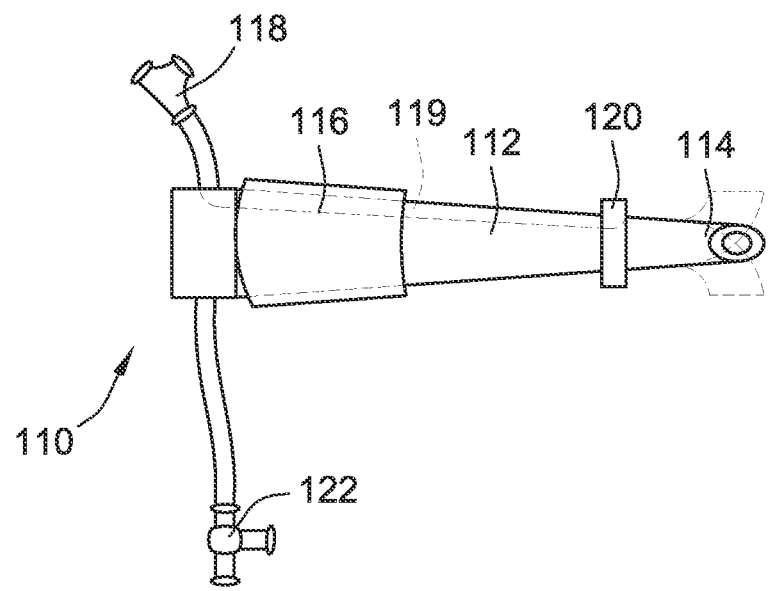
FIG. 2A schematically illustrates a dialysis sheath in accordance with the present invention that is usable in a dialysis flow tube.
Figure 2B:
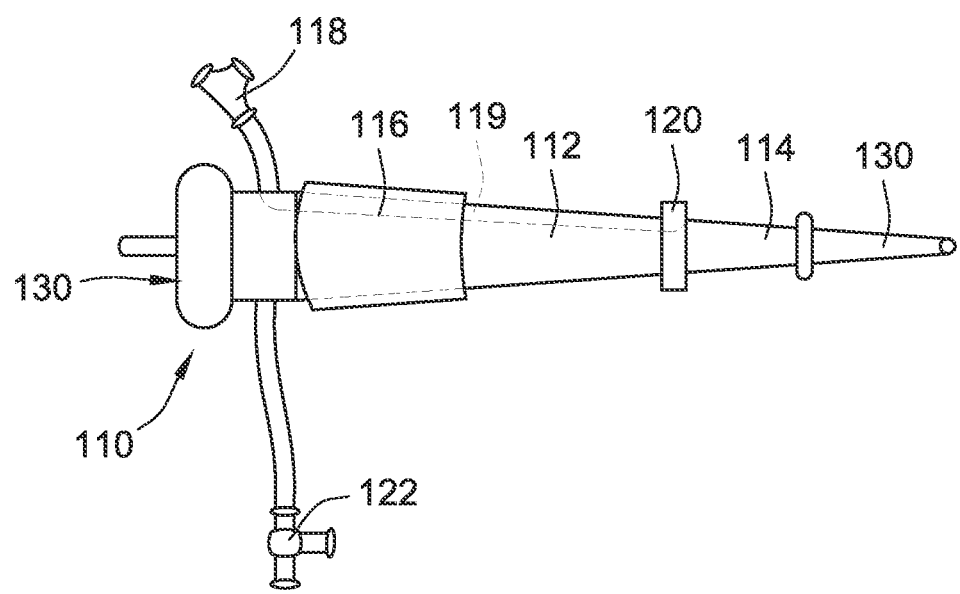
FIG. 2B schematically illustrates the dialysis sheath of FIG. 2A with a dilator inserted.

The dialysis sheath 110 includes a port 118 that is connected by a channel or passage 119 (shown in dashed lines) to a balloon-actuated stop mechanism 120 within the lower portion 114. As shown in FIGS. 2A and 2B, the stop mechanism 120 is actuated and extends radially outward from the main body 112 and serves the purpose of catching the inside wall of the dialysis flow tube 100, as shown in FIG. 5B and described in more detail below. When not actuated, the stop mechanism 120 is located adjacent the exterior walls defining the main body 112. In one embodiment, the stop mechanism 120 may be located partially within a circumferential recess (not shown) on the main body 112. When actuation is needed, the clinician supplies a fluid to the port 118, which pressurizes the fluid passage 119, causing the stop mechanism 120 to expand radially. In one embodiment, the fluid may be a liquid in the form, such as a saline solution, a contrast solution, or a saline/contrast solution. In a further embodiment, the fluid may a gas, such as air.

In an alternative embodiment, the stop mechanism 120 can be a solid resilient structure (e.g., an O-ring) that resiliently expands outwardly under the force of expansion of a balloon-like (or bladder-like) structure on or within the main body 112 when a fluid is moved into and/or pressurized from the port 118. The stop mechanism 120 preferably extends circumferentially 360° around the main body 112, but can extend less than 360° (e.g., 300°) around the main body 112. The stop mechanism 120 can also be a plurality of small independent projections that radially protrude from the main body 112.

In a further alternative, the stop mechanism 120 moves to the extended position under the force of a mechanical device, instead of pressure from a fluid. For example, a cam-like structure is located in a recess of the main body 112 and is connected to a rotatable rod that extends along the main body 112 of the sheath 110. When the rod is actuated, the cam-like structure rotates to a different position, causing the stop mechanism 120 (e.g., an O-ring coupled to the cam-like structure) to move radially away from the main body 112 of the sheath 110.

The sheath 110 also includes a common fluid port 122 for introducing various fluids to the patient's blood stream. The port 122 is connected to a 3-way stopcock that allows introduction of medications, intravenous fluids, or contrasted agents.

The sheath 110 can be mated with a removable dilator 130 that extends through the hollow inner opening of the main body 112 of the sheath 110, as shown in FIG. 2B. The dilator 130 is used in the initial placement of the sheath 110 that is performed over an access wire that gains initial access to the dialysis flow tube 100. The dilator serves to gradually expand the opening in the sheath 110 as it is gradually inserted into the dialysis flow tube 100. Once access of the sheath 110 into the dialysis flow tube 100 is obtained, the dilator 130 is removed while maintaining the sheath 110 within the opening in the dialysis flow tube 100 and positioned over the wire. In some instances, the wire may remain in place. In other instances, the wire can be removed.

Figure 3A:
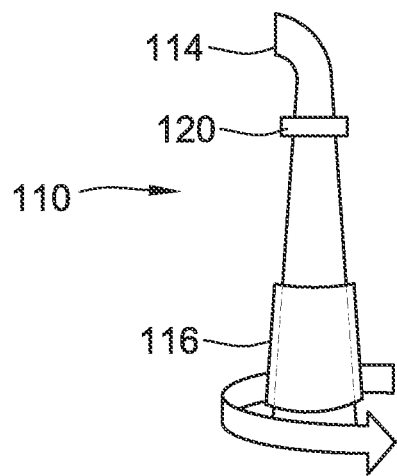
FIG. 3A schematically illustrates the steerable movement of the lower end of the dialysis sheath of FIG. 2A.
Figure 3B:
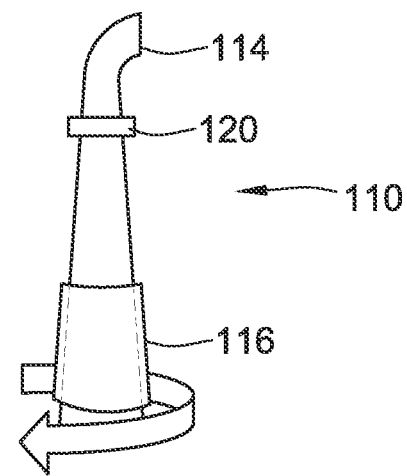
FIG. 3B schematically illustrates further steerable movement of the lower end of the dialysis sheath of FIG. 2A.

FIGS. 3A-3B schematically illustrate the dialysis sheath 110 in FIG. 2A-2B being turned in one direction and the other direction. When the actuator portion 116 is rotated CCW, the steerable lower portion 114 slightly bends or turns in one direction. When the actuator portion 116 is rotated CW, the steerable lower portion 114 slightly bends or turns in the other direction. Steerable sheaths are known to skilled artisans who use sheaths for medical procedures, especially intravenous procedures. Examples of steerable sheaths that have a lower portion that bend include the TourGuide™ steerable sheath from Medtronic, which includes a rotating collar that creates the bending of the lower portion of the sheath. The actuator portion 116 of the present invention may include such a rotating collar to create the bending.

Figure 4A:
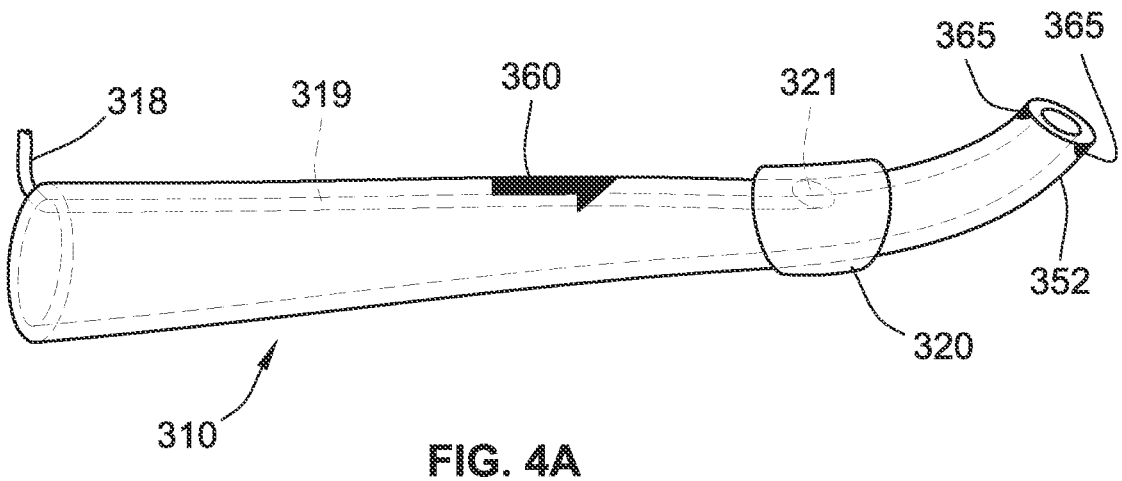
FIG. 4A schematically illustrates a preformed curved sheath in accordance with the present invention that is usable with an AV graft or fistula.
Figure 4B:
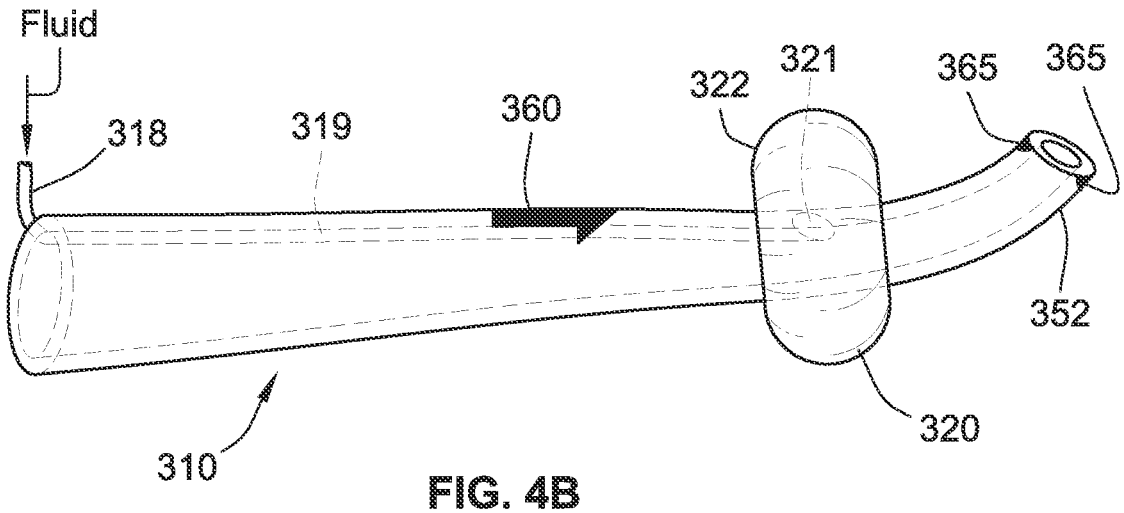
FIG. 4B schematically illustrates the preformed curved sheath of FIG. 4A after actuation of a balloon-actuated stop mechanism.
Figure 4C:
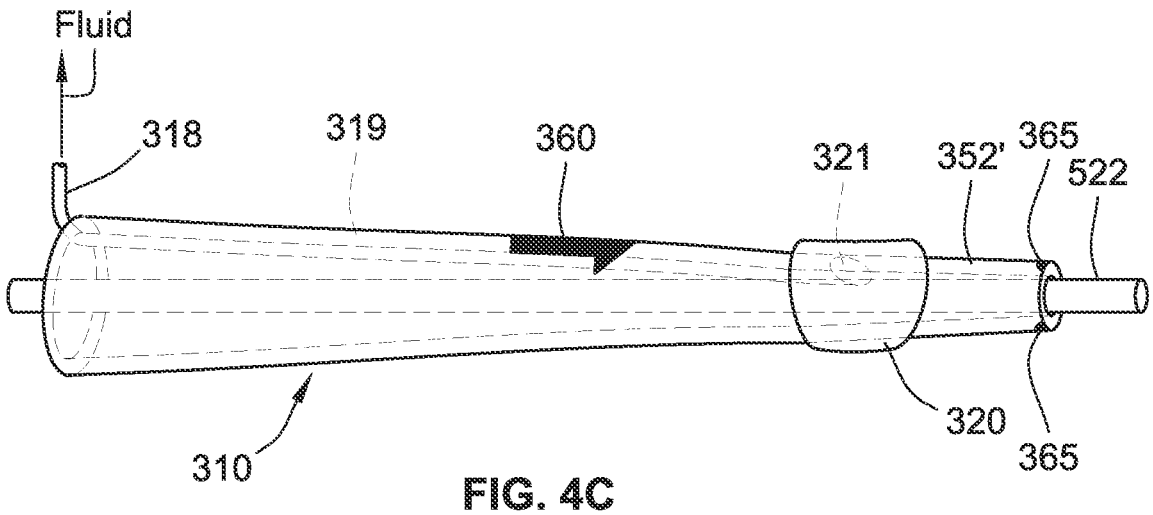
FIG. 4C schematically illustrates the preformed curved sheath of FIG. 4A after a suction catheter has been inserted through it.

FIGS. 4A-4C schematically illustrates a non-steerable sheath 310 that lacks the manual actuator (e.g., actuator portion 116 in FIGS. 2-3). The sheath 310 includes a stop mechanism 320, similar to the stop mechanism 120 described above. The sheath 310 preferably has a slightly preformed curved end region 352 that helps to guide the direction of a suction catheter 522 (shown in FIG. 4C) when inserted. The stop mechanism 320 is preferably a fluid-actuated balloon stop mechanism (like the one illustrated in FIGS. 2-3), which uses a balloon to engage the inner wall of the dialysis flow tube 100. FIG. 4A illustrates the balloon stop mechanism 320 in a deflated state, which allows the lower end 352 to completely pass into an opening within the dialysis flow tube 100.

FIG. 4B illustrate the balloon stop mechanism 320 in the expanded state after the lower end region 352 of the sheath 310 is located within the dialysis flow tube 100. Fluid is passed into a port 318 and through the fluid tube 319 where it enters an opening 322 on the body of the sheath 310, causing the balloon stop mechanism 320 to transition to the expanded state.

FIG. 4C illustrates the sheath 310 with a suction catheter 522 inserted through the hollow inner opening of the sheath 310. The insertion of the suction catheter 522 causes the sheath to straighten (at least to some extent), such that the curvature of the preformed shape in the sheath 310 is reduced or eliminated. Thus, the lower end region 352' of the sheath 310 is now straighter than the curved lower end region 352 of the sheath 310 in FIGS. 4A and 4B. It should be noted that in some embodiments of the sheath 310, the insertion of the suction catheter 522 into the sheath 310 causes less change (or no change) to the curvature of the lower end region 352.

Because the curved lower end region 352 of the sheath 310 is positioned within the dialysis flow tube 100 such that its direction of curvature cannot be seen, the sheath 310 preferably includes a directional marking 360 that indicates the direction of curvature of the lower end region 352. Thus, if a preformed curvature in the sheath 310 is used, the curvature angle will return after the lower end region 352 has been straightened (such as when the catheter 522 is inserted) and the angle can be visualized via the directional marking 360 by the medical personal performing the procedure. This allows the sheath 310 to be turned and rotated such that the lower end region 352 is pointed in a desired direction by visualizing the directional marking 360 on the exterior of the sheath 310. Though an arrow is shown as the directional marking 360, a darkened line or colored dots may also be used to visualize the direction of the curved lower end region 352. Furthermore, the lowermost portion of the curved lower end region 352 may include radio-opaque markers 365 that can be visualized via common imagining techniques to help locate the lowermost portion of the sheath 310 when it is within the dialysis flow tube 100. The radio-opaque markers 365 and the directional markings 360 may also be used in the other embodiments of the sheathes described with reference to FIGS. 2-3 and FIGS. 7-8.

The balloon stop mechanism 320, which is shown as having a generally toroidal shape, preferably has some level of resiliency and flexibility to assist with sealing the opening in the dialysis flow tube 100 to the escape of blood. The side profile of the balloon stop mechanism 320, as shown in FIG. 4B can have varying shapes, such that its uppermost surface 322 is somewhat rounded. When the balloon stop mechanism 320 is expanded, the upper surface 322 can also be configured with a flattened shape with sharper corners. Furthermore, because the dialysis flow tube 100 is generally tubular in shape with some level of curvature, the upper surface 322 may have a slight saddle shape to better engage the curved inner surface of the dialysis flow tube 100 around the opening to better seal the opening in the dialysis flow tube 100 in which the sheath 310 has been inserted.

Alternatively, the stop mechanism 320 may use a balloon-like mechanism that, under the movement or pressure of a fluid, force a structure (e.g., a flexible O-ring) outwardly beyond the outer surface of the sheath 310 such that the structure engages the inner wall of the dialysis flow tube 100. In a further alternative, the stop mechanism 320 in FIGS. 4A and 4B may incorporate a mechanical actuator (e.g., a cam structure) to move a structure (e.g., a flexible O-ring) outwardly beyond the outer surface of the sheath 310 such that the structure engages the inner wall of the dialysis flow tube 100.

Figure 5A:
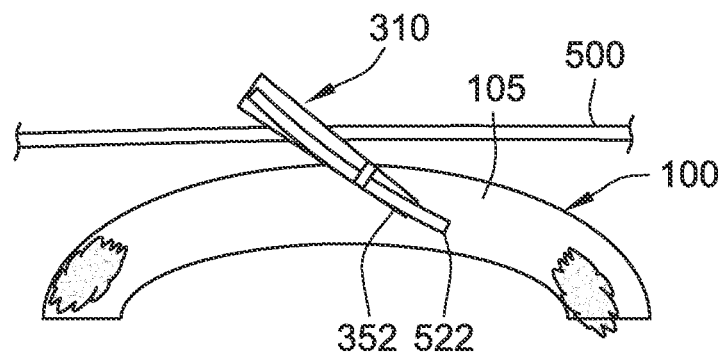
FIG. 5A schematically illustrates a dialysis sheath of FIGS. 4A-4C in accordance with the present invention in use with a catheter cleaning a clot from one side of a dialysis flow tube.
Figure 5B:
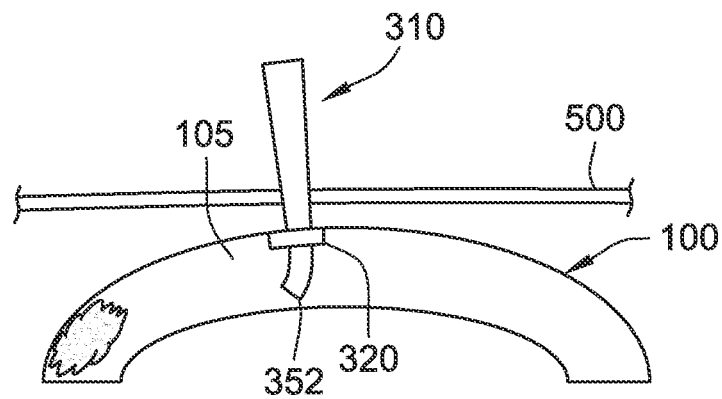
FIG. 5B schematically illustrates the dialysis sheath of FIGS. 4A-4C with the stop mechanism engaging the wall of the dialysis flow tube.
Figure 5C:
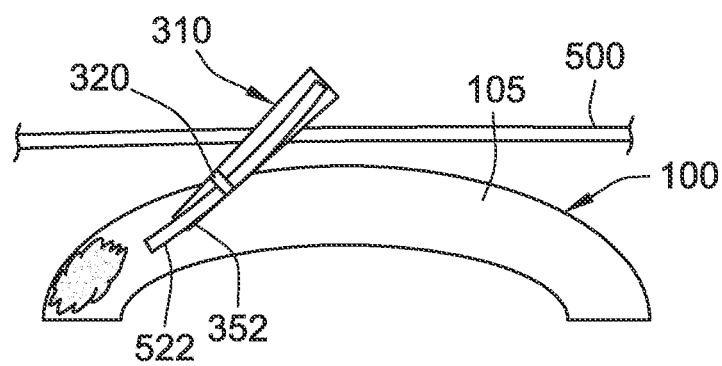
FIG. 5C schematically illustrates the dialysis sheath of FIGS. 4A-4C in use with a catheter cleaning clots from the dialysis flow tube in a different direction relative to FIG. 5A.

FIGS. 5A-5C illustrate the sheath 310 when used to assist with clearing clots from the dialysis flow tube 100 that resides below the skin tissue 500. Initially, the dialysis flow tube 100 is typically accessed with a needle and an access wire in the curved middle portion 105. This initial part of the procedure is preferably performed under ultrasound guidance to ensure correct access. Following the access with the needle, the access wire is exchanged for another slightly larger wire (e.g., 0.035 wire) and the needle is removed. The opening is then preferably dilated with a dilator (such as dilator 130 in FIGS. 2A and 2B) to the appropriate size and the sheath 310 is inserted into dialysis flow tube 100. In one embodiment, the dilator and the sheath 310 are inserted together over the wire and, once the sheath 310 is advanced to the preferred location in the dialysis flow tube 100, the dilator is removed. When the preformed sheath 310 is used with a dilator, the curvature at the lower end 352 is typically straightened. However, once the dilator is removed, the preformed curvature at the lower end of the sheath 301 then returns.

Next, as shown in FIG. 5A, a suction catheter 522 is inserted into the sheath 310 and cleans the dialysis flow tube 100 in a first direction (shown to the right in FIG. 5A). Once cleaning in the first direction is complete, the stop mechanism 320 is actuated, as described above. Preferably before the suction catheter 522 is fully or partially retracted from the sheath 310, the stop mechanism 320 is actuated to engage the inner wall of the dialysis flow tube 100 and to prevent the sheath 310 from being fully withdrawn from the dialysis flow tube 100, as shown in FIG. 5B. If the sheath 310 were to be fully withdrawn from the dialysis flow tube 100, blood would begin flowing out of the dialysis flow tube 100 and below the patient's skin (and perhaps outside the patient's skin). With no wire or suction catheter 522 extending through the sheath 310, the lower end region 352 of the sheath 310 returns to its normal curved shape and can be manipulated so as to point in the opposite direction. Once the sheath 310 is manipulated to the opposite direction, as shown in FIG. 5C, the catheter 522 can be reinserted (over a working wire or without a wire) and the catheter 522 cleans the dialysis flow tube 100 in the other direction. The lower end region 352 of the sheath 310 is straightened when the suction catheter 522 is reinserted for cleaning the left side of the dialysis flow tube 100.

The stop mechanism 320 on the sheath 310 permits the forces associated with the retraction of the catheter 522 and the physical manipulation of the sheath 310 to be counteracted by the engagement of the stop mechanism 320 against the inner wall of the dialysis flow tube 100. As such, the patient's blood is more readily maintained within the dialysis flow tube 100. And unlike current practice, there is only a single access hole required to clean in both directions.

Though FIGS. 5A-5C illustrate the sheath 310 of FIGS. 4A-4B having the lower end region 352 (which is preferable slightly curved), the steerable sheath 110 with the stop mechanism 120 and the steerable lower portion of FIGS. 2-3 works in the same manner as the stop mechanism 320 of the sheath 310 of FIGS. 4-5. The stop mechanism 120 maintains the sheath 110 of FIGS. 2-3 within the dialysis flow tube 100 when the forces associated with the retraction of the catheter 522 and/or the physical manipulation of the sheath 110 are encountered.

The dimensions of the sheaths 110, 310 are typically 6 Fr to 8 Fr. ("Fr" being the French system commonly used for measuring catheters in which 3 Fr=1 mm). Thus, the outer diameter of the sheath 110, 310 would be approximately in the range of 2.6 mm to 3.0 mm, whereas the inner tip diameter of the sheath 110, 310 would be in the range of approximately 2.0 mm to 2.7 mm. The sheaths 110, 310 would work over a wire (e.g., 0.035 wire). The overall length of the sheaths 110, 310 would be approximately 10 cm or as short as possible to hold the steerable technology and the stop mechanism 120, 320. The stop mechanism 120, 320 would expand upon deployment to have a diameter that is approximately 1.5 to 2.0 times the outer diameter of the sheath 110, 310 in that region of the sheath 110, 310.

Figure 6A:
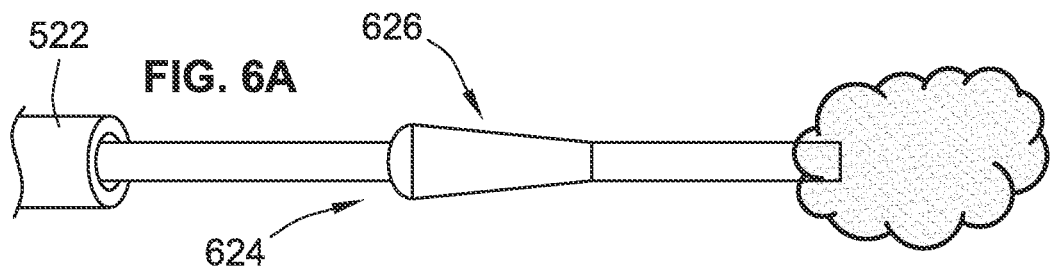
FIG. 6A illustrates a first embodiment of separator wire that can be used with the dialysis sheaths noted above.

In addition to suction catheters 522, it should be understood that separator wires can be used with the suction catheter 522 and the sheath 110, 310 to remove blood clots within any blood vessels and also the dialysis flow tube 100. As described relative to FIGS. 6A-6E, a separator wire 624 may be located within the suction catheter 522 and can be advanced and retracted by the clinician who has access to the proximal end of the separator wire 624 that is located outside of the patient's body. The separator wire 624 includes a separator element 626 located just short of or within the distal end region of the separator wire 624. In the advancement and retraction process, the distal end engages the clot to help break it apart so that pieces of the clot can be suctioned within the blood vessel or dialysis flow tube 100 toward and eventually into the catheter 522. The separator element 626 further helps to break apart the 15 as well. In known systems, the separator element 626 has more of a bullet shape, which may include a straight tapered or curved tapered outer surface, as shown in FIG. 6A. The major surface of the separator element 626 tapers outwardly away from the distal end to a point that has a major diameter, at which the separator element 626 has a reverse taper. Though useful, the shape of the separator element 626 on its back side does not perform a high level of disrupting of the clot to break it apart.

Figure 6B:
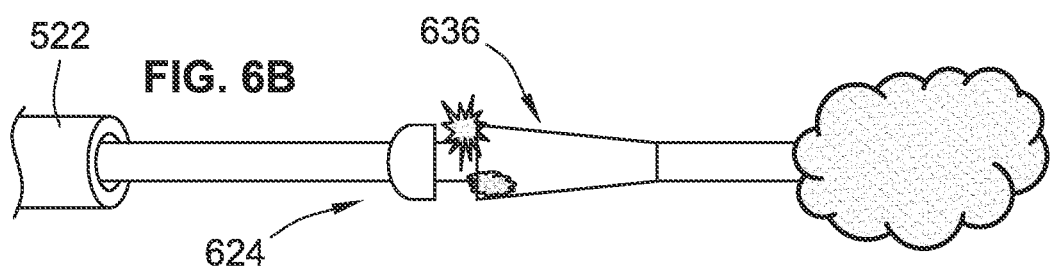
FIG. 6B illustrates a second embodiment of separator wire that can be used with the dialysis sheaths noted above.

FIG. 6B-6E illustrate of an improved separator element 636 for use on the separator wire 624 in accordance with one embodiment of the present invention. The major tapering surface at the distal portion of the separator element 636 has been broken to create a circumferential groove. The back surface of the distal portion of the separator element 636 is generally flat. The back apical portion of the separator element 636 has a curved, short surface leading back to the diameter of the separator wire 624. Consequently, when the separator wire 624 is advanced by the clinician into the clot, the subsequent retraction motion will cause pieces of the clot to be caught on the edges of the separator element 636 adjacent to the circumferential groove, as shown in FIG. 6B. The pieces will then be pulled back toward and enter the catheter 522 (FIGS. 5A-5C) via the suctioning process. The atraumatic cone-shaped front distal portion of the separator element 636 has a secondary ridge or ridges to better free blood vessels and synthetic blood vessels (e.g., dialysis grafts) from chronic thrombus and atherosclerotic disease.

Figure 6C:
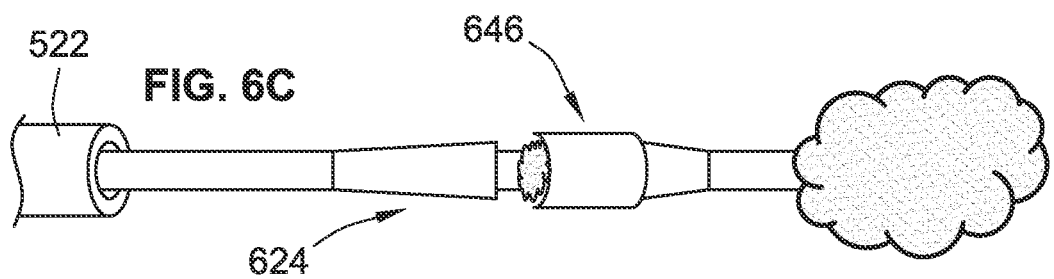
FIG. 6C illustrates a third embodiment of separator wire that can be used with the dialysis sheaths noted above.

FIG. 6C illustrates another improved separator element 646 for use on the separator wire 624 in accordance with another embodiment of the present invention. In this embodiment, the circumferential groove is located in the separator element 646. However, the back edge of the front portion of the separator element 646 has a concave shape (or has portions with concave shapes) to create an edge or ridge (or edges or ridges) that help to grasp pieces of the blood clot during retraction of the separator wire 624. Further, relative to the separator element 636 of FIG. 6B, the back proximal portion of the separator element 646 is more elongated and has a straight taper surface leading back to the diameter of the separator wire 624. Like FIG. 6B, the atraumatic cone-shaped front distal portion of the separator element 646 has secondary ridges to better free vessels and grafts from chronic thrombus and atherosclerotic disease.

Figure 6D:
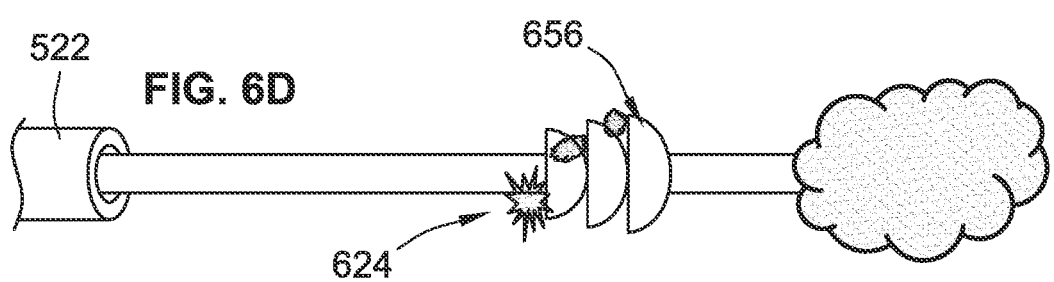
FIG. 6D illustrates a fourth embodiment of separator wire that can be used with the dialysis sheaths noted above.

FIG. 6D illustrates a further embodiment of the separator element 656 for use of the separator wire 624 in accordance with a further embodiment of the present invention. Here, the separator element 656 comprises a series of short, rounded cones that create a series of edges that help to capture and pull back pieces of clot. Grooves are located between the edges. The series of short, rounded cones of the separator element 656 increase in dimension toward the distal end of the separator wire 624. The series of rounded cones would be flexible and atraumatic, but sturdy enough for successful thrombectomy of blood vessels (and also PTFE and dacron synthetic grafts).

Figure 6E:
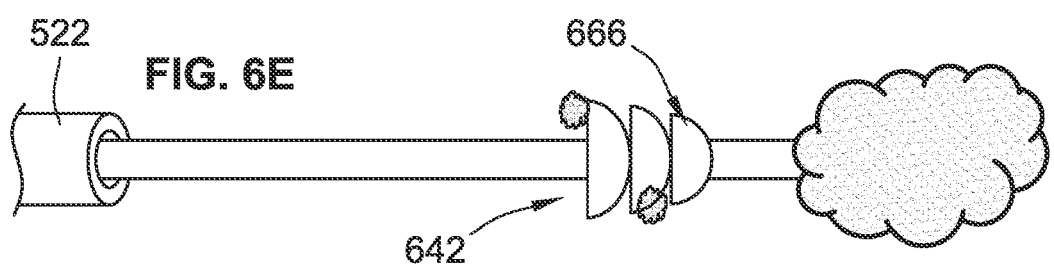
FIG. 6E illustrates a fifth embodiment of separator wire that can be used with the dialysis sheaths noted above.

FIG. 6E illustrates yet a further embodiment of the separator element 666 for use of the separator wire 624 in accordance with a further embodiment of the present invention. Like the separator element 656 of FIG. 6D, the separator element 666 includes a series of short, rounded cones that create a series of edges or ridges that help to capture and pull back pieces of clot. However, the series of short, rounded cones of the separator element 666 decrease in dimension toward the distal end of the separator wire 624. In accordance with a further embodiment, the separator element 666 may comprise a second series of short, rounded cones that are arranged in the manner of FIG. 6E such that wire includes rounded cones facing in both directions.

Though the separator elements 636, 646, 656, 666, of FIGS. 6A-6E are described as useful in working with the dialysis sheathes 110, 310 (and those in FIGS. 7-8 below), they are useful in other procedures as well.

The present invention contemplates separator elements having a variety of shapes created by grooves, undercuts, and/or tapered surfaces that assist with breaking apart the clot with edges or ridges and capturing pieces of the clot within recesses or regions on the separator element so as to pull those removed pieces of the clot toward the suctioning catheter 522 in response to the clinician manually retracting the separator wire 624. The separator elements may further include other geometries such as a series of protuberances or projections on the surface of the separator element that are spaced by recesses. The series of protuberances or projections can be circumferentially arranged, linearly arranged in the distal-proximal direction, helically arranged along the surface of the separator element, or a combination thereof.

The material of the separator wires 624 is preferably Nitinol. The material for the separator elements 626, 636, 646, 656, and 666 is preferably an atraumatic synthetic polymer and can be used on a 0.014-0.038 wire system (0.36-0.97 mm) and have working lengths of 20-50 CM for use with the sheath 110, 310 of FIGS. 2-5, and from 50 cm to 190 cm for uses that require deeper insertion into the patient's vascular system. The polymeric material of the separator elements 626, 636, 646, 656, and 666 preferably has some elasticity so that it can flex. The distal end portion of the separator element tapers in the proximal direction and all ridges, edges, protuberances, projections preferably have a smaller diametric dimension than the maximum diameter of the distal end portion (i.e., the ridges, edges, protuberances, projections defining the grooves are preferably sunk below the distal end portion).

The present invention also entails a method of using multiple separator wires 624 having different types of separator elements 626, 636, 646, 656, and 666. In response to a separator wire 624 with the basic separator element 626 not performing as planned to remove the clot, the clinician chooses a different separator wire 624 from among a plurality of separator wires 624, each of which has a different type of separator element that is better suited for removing the clot based on the prevailing conditions of the vein or artery. For example, the separator wire 624 with the separator element 626 is first introduced into the suction catheter 522, and then the separator wire 624 with the separator element 636 may be subsequently introduced to help remove the clot. If that does not achieve the desired outcome, the method and kit permits the clinician to select yet a further separator wire 624 with the separator element 636, 646, 656, or 666 based on the conditions.

Although the separator wires 624 with the differently shaped separator elements 636, 646, 656, or 666 in FIGS. 6B-6D have been described as being used in conjunction with the novel sheathes 110, 310 for cleaning the dialysis graft 100, these separator wires 624 with the differently shaped separator elements 636, 646, 656, or 666 have other uses throughout the body. Hence, the present invention also includes the apparatuses and methods involving the separator wires 624 with the differently shaped separator element 636, 646, 656, or 666 and uses thereof that are independent of cleaning dialysis grafts (as described above) and independent of the novel sheathes 110, 310, 710, 810 described herein.

A separator wire for use with a suction catheter, comprises an elongated wire having a proximal end that can manipulated outside a patient's body and a distal end for placement within a blood vessel or a synthetic blood vessel. The separator wire includes a separator element located near the distal end of the elongated wire. The separator element has an outer surface with a groove defining an edge or ridge for assisting with disrupting a blood clot. In one embodiment, the groove for the separator is for receiving pieces of the blood clot that have been removed from the blood clot. In another embodiment, the outer surface with the groove tapers downwardly toward the distal end of the elongated wire. In a further embodiment, the outer surface with the groove tapers downwardly toward the proximal end of the elongated wire.

In another aspect, a separator wire for use with a suction catheter, comprises an elongated wire having a proximal end that can manipulated outside a patient's body and a distal end for placement within a blood vessel or a synthetic blood vessel. The separator wire further includes a separator element located near the distal end of the elongated wire. The separator element has a discontinuous outer surface that defines an edge or ridge for assisting with disrupting a blood clot. In one embodiment, the discontinuous outer surface creates a groove that receives pieces of the blood clot that have been removed from the blood clot. In a further embodiment, the discontinuous outer surface tapers downwardly toward the distal end of the elongated wire. In yet a further embodiment, the discontinuous outer surface tapers downwardly toward the proximal end of the elongated wire. The discontinuous outer surface may be formed by a series of protuberances or projections on the other surface. The discontinuous outer surface may also be formed by a series of cone-like surfaces.

In another aspect, a kit of separator wires for use with a suction catheter comprises a plurality of separator wires. Each of the plurality of separator wires has a separator element, the separator elements having outer surfaces with different geometric shapes.

A method of clearing a clot from a blood vessel or a synthetic blood vessel comprises (i) inserting a first separator wire into a catheter, the first separator wire having first separator element for engaging the clot; and (ii) in response to the first separator wire not removing all of the clot, inserting a second separator wire into the catheter, the second separator wire having a second separator element for engaging the clot, the second separator element having a different geometric configuration than the first separator element.

Referring now to FIGS. 7A-7B, an alternative sheath 710 includes an outer portion 715 and an inner portion 718 that is movable relative to the outer portion 715. The inner portion 718 includes a stop mechanism 720 that contracts against the inner surface of the outer portion 715 when located therein. However, when the both the outer portion 715 and the inner portion 718 are within the graft 100 and the inner portion 718 is then moved forward relative to the outer portion 715, the stop mechanism 720 resiliently expands outwardly once it is beyond the tip of the outer portion 715, as shown in FIG. 7B. The resilient stop mechanism 720 then engages the inner surface of the dialysis flow tube 100 to help retain the sheath 710 in the graft 100 while the sheath 710 and/or catheter is being manipulated. Conversely, when the inner portion 718 is pulled back into the outer portion 715, the stop mechanism 720 resiliently contracts and is again located between the inner portion 718 and the outer portion 715, as shown in FIG. 7A.

It is also contemplated that a lower region 752 of the inner portion 718 of the sheath 710 includes a preformed curved shape (similar to the sheath 310 of FIG. 4) such that, when it is outside of the outer portion 715, it reverts to its preformed curved shape. The suction catheter 522 can be inserted through the inner portion 718 to clear the clots within the dialysis flow tube 100. Though not shown in FIG. 7B, in some embodiments, the suction catheter 522 may cause the curved lower region 752 of the inner portion 718 to straighten when inserted through the curved lower region 752 (as shown in FIG. 4C).

FIGS. 8A-8B illustrate an alternative sheath 810 that includes a mechanical stop mechanism 820 that fits along the external side surfaces of the sheath 810. In some embodiments, the mechanical stop mechanism 820 may also be located within a recess or recesses in the external side surfaces of the sheath 810. The stop mechanism 820 can be a rigid plate or structure or a flexible or resilient element.

The sheath 810 includes an actuator handle 830 that, when manipulated (e.g., pulled away from the sheath 810 or rotated) causes an actuator rod or line 832 to move, thereby causing movement of the stop actuator arms or lines 834a, 834b. The stop actuator arms or lines 834a, 834b cause the stop mechanism 820 to move radially outwardly to engage the inner wall of the dialysis flow tube 100 as shown in FIG. 8B. The opposite movement of the actuator handle 830 causes the stop mechanism 820 to move back against the outer surface of the sheath 810, as shown in FIG. 8A.

These embodiments and obvious variations thereof is contemplated as falling within the spirit and scope of the claimed invention, which is set forth in the following claims. Moreover, the present concepts expressly include any and all combinations and subcombinations of the preceding elements and aspects.

I claim:

1. A dialysis sheath for use with a catheter that cleans obstruction from a dialysis flow tube used for dialysis of a patient, comprising:
   a main hollow body having a lower portion for insertion into an opening of the dialysis flow tube, the main hollow body for guiding the catheter that enters into the dialysis flow tube for cleaning obstructions;
   a fluid passage extending along the main hollow body; and
   a fluid-actuated stop mechanism positioned within the lower portion of the main hollow body, the fluid-actuated stop mechanism being in communication with the fluid passage, the fluid-actuated stop mechanism being actuatable to transition between (i) a first position in which the stop mechanism is adjacent to or within a surface of the lower portion of the main hollow body, and (ii) a second position in which the stop mechanism expands to radially protrude away from the main hollow body so as to be configured to engage an inner surface of the dialysis flow tube directly adjacent to the opening to maintain the lower portion of the main hollow body within the dialysis flow tube, and
   wherein, in response to the fluid-actuated stop mechanism being in the second position, the fluid-actuated stop mechanism is configured to anchor the lower portion of the main hollow body within the dialysis flow tube while the dialysis sheath is being manipulated to change a direction of the lower portion.

2. The dialysis sheath of claim 1, further including a manual actuator that changes the direction of the lower portion in response to being actuated.

3. The dialysis sheath of claim 1, wherein the lower portion has a fixed shape.

4. The dialysis sheath of claim 1, wherein the lower portion has a preformed curved shape.

5. The dialysis sheath of claim 4, wherein the preformed curved shape of the lower portion transitions to a straighter lower portion in response to the catheter being inserted through the lower portion of the main hollow body.

6. The dialysis sheath of claim 1, wherein the stop mechanism includes a balloon mechanism, the stop mechanism expands into the second position in response to the fluid passing through the fluid passage.

7. The dialysis sheath of claim 6, wherein the balloon mechanism is configured to engage the inner surface of the dialysis flow tube without obstructing the blood flow.

8. The dialysis sheath of claim 7, wherein the balloon mechanism extends entirely around the lower portion of the main hollow body.

9. The dialysis sheath of claim 8, wherein the balloon mechanism has a toroidal shape.

10. The dialysis sheath of claim 7, wherein the balloon mechanism extends radially outwardly for less than 360° around the lower portion.

11. The dialysis sheath of claim 7, wherein the lower portion has a preformed curved shape, the preformed curved shape of the lower portion transitions to a straighter lower portion in response to the catheter being inserted through the lower portion of the main hollow body.

12. The dialysis sheath of claim 6, wherein the stop mechanism further includes a solid element that moves outwardly to the second position in response to the expansion of the balloon mechanism, the solid element for engaging the inner surface of the dialysis flow tube.

13. The dialysis sheath of claim 12, wherein the solid element includes an O-ring that is adjacent to the balloon mechanism.

14. The dialysis sheath of claim 1, wherein the fluid passage is defined by material of the main hollow body.

15. The dialysis sheath of claim 14, wherein the fluid passage is located adjacent to an inner surface of the main hollow body.

16. A method of clearing a clot from a dialysis flow tube that is used for dialysis, the method comprising:
   inserting a sheath into an opening in the dialysis flow tube;
   inserting a catheter through the sheath for cleaning the dialysis flow tube in a first direction relative to the opening;
   using a fluid to expand a stop mechanism associated with the sheath such that the stop mechanism protrudes radially away from the sheath;
   without removing the sheath from the opening, engaging the expanded stop mechanism to an internal surface of the dialysis flow tube, the internal surface being located directly adjacent to the opening in the dialysis tube, the stop mechanism for assisting with maintaining the sheath within the dialysis flow tube;
   while the stop mechanism is engaging the internal surface of the dialysis flow tube directly adjacent to the opening in the dialysis tube, manipulating the direction of a lower end of the sheath within the dialysis flow tube; and
   after the manipulating, using the catheter to clean the dialysis flow tube in a second direction relative to the opening, the second direction being opposite to the first direction.

17. The method of claim 16, wherein the stop mechanism includes a balloon mechanism that receives a volume of fluid to expand the balloon mechanism.

18. The method of claim 17, wherein the engaging includes contacting the balloon mechanism within the internal surface of the dialysis flow tube when the balloon is in expanded.

19. The method of claim 16, wherein the using the fluid causes a solid element of the stop mechanism to move outwardly from the outer surface sheath, the solid element for engaging the internal surface.

20. The method of claim 16, wherein the sheath has a preformed curved shape at a lower portion thereof, wherein the reinserting of the catheter transitions the curved shape to a straighter lower portion.

* * * * *